US007286863B2

(12) United States Patent
Leonhardt et al.

(10) Patent No.: US 7,286,863 B2
(45) Date of Patent: Oct. 23, 2007

(54) DEVICE AND PROCESS FOR PUTTING AN ELECTRODE CARRIER ON A PATIENT

(75) Inventors: Steffen Leonhardt, Lübeck (DE); Eckhard Teschner, Hamburg (DE); Dieter Sahmkow, Lübeck (DE); Hans-Wilhelm Steen, Zarpen (DE); Hans Matthiessen, Bad Schwartau (DE); Yvo Gärber, Lübeck (DE); Karsten Hoffmann, Griebel (DE); Jianhua Li, Lübeck (DE); Rainer Degenhart, Stockelsdorf (DE); Markus Hampe, Lübeck (DE)

(73) Assignee: Dräger Medical AG & Co. KGaA (DE)

( * ) Notice: Subject to any disclaimer, the term of this patent is extended or adjusted under 35 U.S.C. 154(b) by 435 days.

(21) Appl. No.: 10/851,718

(22) Filed: May 20, 2004

(65) Prior Publication Data

US 2005/0033134 A1 Feb. 10, 2005

(30) Foreign Application Priority Data

Jul. 30, 2003 (DE) ................................ 103 34 669

(51) Int. Cl.
*A61B 5/04* (2006.01)

(52) U.S. Cl. ...................................................... 600/372
(58) Field of Classification Search ................ 600/372
See application file for complete search history.

(56) References Cited

U.S. PATENT DOCUMENTS 2,099,977 A * 11/1937 Harris ........................ 27/21.1
3,323,514 A * 6/1967 Barrett, Jr. .................. 600/508
5,287,577 A 2/1994 Bremer et al.
5,713,841 A * 2/1998 Graham ....................... 602/32

FOREIGN PATENT DOCUMENTS

EP 0 448 555 10/1991

* cited by examiner

*Primary Examiner*—Lee S. Cohen
(74) *Attorney, Agent, or Firm*—McGlew and Tuttle, P.C.

(57) ABSTRACT

A device is provided for putting an electrode carrier on a recumbent patient. The device includes a first lifting cushion that supports the shoulder region and the head of the patient at the same time and into which a pressurized medium can be admitted. A second lifting cushion is provided that supports the lumbar region and into which pressurized medium can be admitted. A spacer is provided fixing the lifting cushions in relation to one another in the chest region.

9 Claims, 1 Drawing Sheet

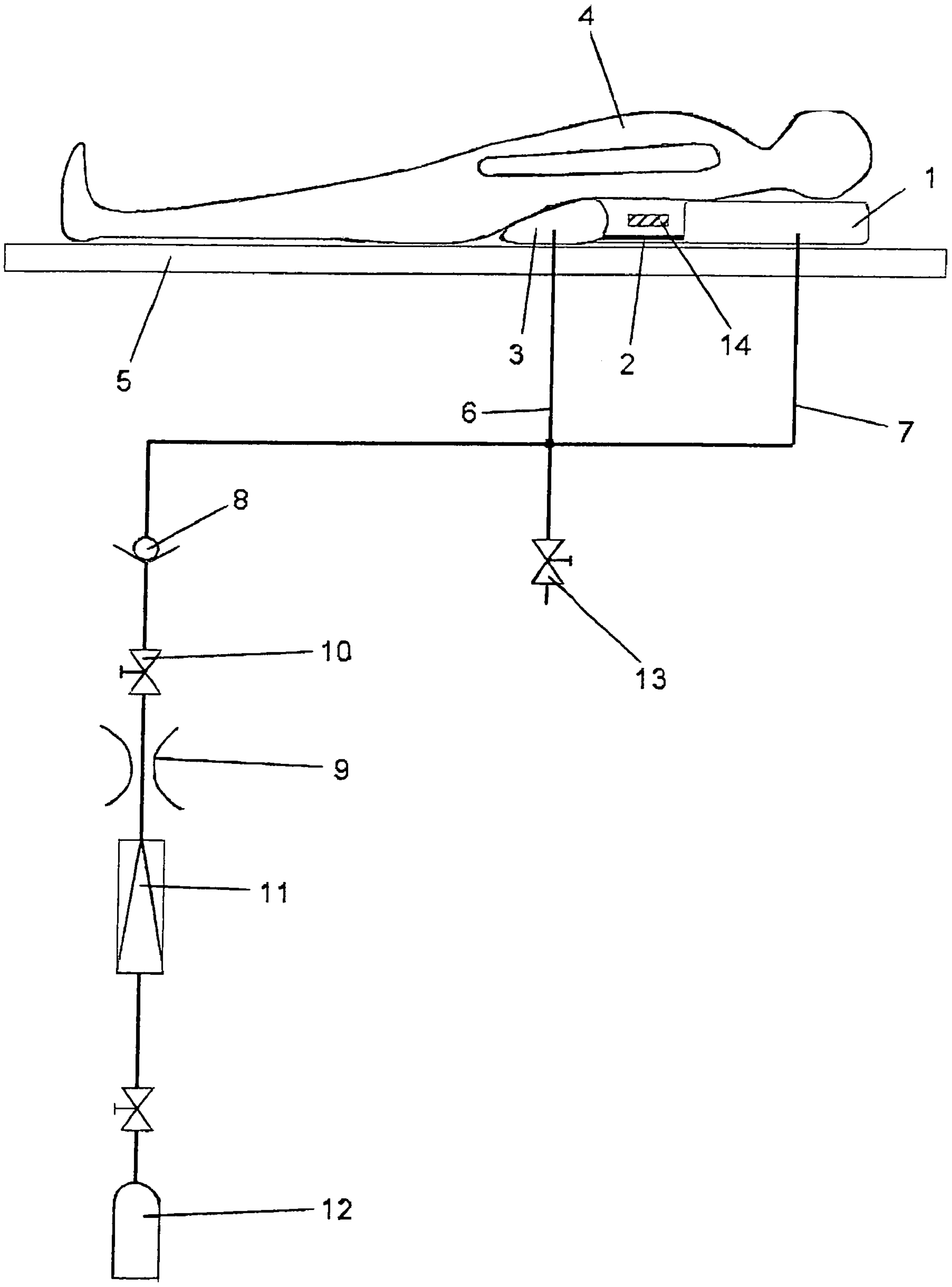
4
1
3
2
14
5
6
7
8
13
10
9
11
12

DEVICE AND PROCESS FOR PUTTING AN ELECTRODE CARRIER ON A PATIENT

CROSS REFERENCE TO RELATED APPLICATIONS

This application claims the benefit of priority under 35 U.S.C. § 119 of German patent application DE 103 34 669.4 filed Jul. 30, 2003, the entire contents of which are incorporated herein by reference.

FIELD OF THE INVENTION

The present invention pertains to a device and a process for putting an electrode carrier on a patient.

BACKGROUND OF THE INVENTION

It is necessary in a number of medical diagnostic procedures to place electrodes on the body of a patient. If the measuring points are located in readily accessible areas with the patient in the recumbent position, for example, in the chest area, the electrodes can usually be fastened without any major difficulties. For certain measuring procedures, such as electric impedance tomography (EIT), an electrode carrier with, e.g., 16 or 32 electrodes must be placed around the patient's chest in order to make it possible to measure the surface potentials along a section plane through the patient's body. Such a tomogram of the impedance distribution is used to visualize and monitor the ventilation of the lung as well as the blood or serum shift in a regionally resolved manner.

The placement of the electrode carrier does not usually cause any problems in case of mobile patients who can raise their upper bodies themselves. By contrast, it is difficult to fasten an electrode carrier extending around the chest in case of respirated patients lying unconscious in bed. This is usually possible only by turning the patient several times. Such a manipulation is highly burdensome in case of severely ill patients for both the health care personnel and the patient.

It is known that variable-pressure cushions are placed on the bed for bedridden patients in order to prevent decubital necroses on the back. In prior-art variable-pressure cushions, pressure is alternatingly admitted into two groups of cells located close next to each other. A reversing valve connects a pressurized gas source with one of the cell groups each, while the other cell group is depressurized. A massaging effect and stimulation of the blood circulation are achieved as a result. A novel variable-pressure cushion is known from EP 448 555 B1. The prior-art variable-pressure cushion is designed for dynamic applications with short pressure change cycles.

SUMMARY OF THE INVENTION

The basic object of the present invention is to provide a device and a process for putting an electrode carrier on a recumbent patient.

According to the invention, a device is provided for putting an electrode carrier on a recumbent patient. The device includes a first lifting cushion that supports the shoulder region and the head of the patient at the same time and into which a pressurized medium can be admitted. A second lifting cushion is provided that supports the lumbar region and into which pressurized medium can be admitted. A spacer is provided fixing the lifting cushions in relation to one another in the chest region.

According to another aspect of the invention, a process is provided for putting an electrode carrier on the chest of a patient. Two lifting cushions are arranged at spaced locations from one another under the patient. A pressurized medium is admitted into the lifting cushions in order to lift the patient. The electrode carrier is pulled through the free space formed between the lifting cushions.

According to another aspect of the invention, a process is provided for use of two lifting cushions. The lifting cushions are arranged at spaced locations from one another for lifting a patient for placing a electrode carrier in the free space between the lifting cushions.

The advantage of the present invention is essentially that the patient can first be lifted for putting on the electrode carrier and then lowered by a first lifting cushion that supports the shoulder region and the head at the same time as well as a second lifting cushion, which is located in the lumbar region and is fixed at a predetermined distance from the first lifting cushion. By admitting pressure into the lifting cushions, the forces necessary for lifting can be applied gently, and the large contact surface of the lifting cushions prevents lowering too deep in case of soft beds.

The lifting cushions are coupled pneumatically, and equal pressure is admitted into them. A hollow channel, through which the electrode carrier can be pulled, is formed in the area of the spacer between the two lifting cushions. The spacer consists of a flexible material and connects the two lifting cushions, so that these cannot change their positions under the patient.

The lifting cushions are shaped ergonomically and have no sharp edges or warps that could cause decubitus necroses in the patient. It is advantageous to coat or line the lifting cushions with fabric or another sweat-draining material. In another advantageous embodiment, the surface relief of the lifting cushions is rippled in order to drain off sweat, on the one hand, and to prevent the skin from sticking to the cushion, on the other hand.

It is also possible to divide the lifting cushions into individual, interconnected cells in order to achieve a higher mechanical stability.

The lifting cushions are filled with a gas or a liquid, a typical filling pressure being about 200 mbar.

The device according to the present invention can also be operated from pressurized gas cylinders, which offers advantages in case of mobile use.

It is advantageously also possible to use an electrically driven blower as the energy source, with which the pressure necessary for filling the lifting cushions is generated by compressing room air. Mechanically or electrically actuated valves may also be used in such an arrangement for filling the lifting cushions or for releasing the air from them.

In an advantageous embodiment of the blower, reverse flow through the blower is possible in the currentless or inoperative state, so that the pressure can be built up in the lifting cushions via the blower, on the one hand, and depressurization of the lifting cushions is possible by switching off the blower, on the other hand. No additional mechanically or electrically actuated valves are needed in this case.

A volume source is used as the energy source in another preferred embodiment. This volume source in the form of a volume displacer may be driven electrically, e.g., as a reciprocating piston compressor or an air pump. A manually actuated foot pump or a bellows is suitable as well.

The cell width of the first lifting cushion is advantageously designed to be such that it is at least twice the cell width of the second lifting cushion. It is achieved as a result that the first lifting cushion can support both the shoulder region and the head region, while the second lifting cushion is in contact in the lumbar region.

The spacer between the lifting cushions advantageously has a width between 5 cm and 15 cm. It is thus possible to pull through the electrode carrier manually under the patient.

The lifting height is designed to be such that the patient can be lifted by more than 5 cm in the area of the spacer.

An advantageous application of two lifting cushions that are arranged at spaced locations from one another and are located under a patient is to lift the patient by admitting pressure into the lifting cushions in order to make it possible to arrange an electrode carrier in the free space between the lifting cushions.

It is especially advantageous to supply the lifting cushions with the pressurized medium via an adjustable pressure reducer. The lifting height of the lifting cushions can be set continuously by changing the back pressure of the pressure reducer, and it is also possible to lift the patient over a longer period of time.

An exemplary embodiment of the present invention is shown in the figure and will be explained in greater detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

BRIEF DESCRIPTION OF THE DRAWINGS

The only FIGURE is a schematic view of the device for putting an electrode carrier on a recumbent patient according to the invention.

DESCRIPTION OF THE PREFERRED EMBODIMENT

The only FIGURE schematically shows a first lifting cushion 1 and a second lifting cushion 3 connected with the first lifting cushion 1 via a spacer 2 between a patient 4 and a patient bed 5. The lifting cushions 1, 3 are connected to a pressurized gas source 12 via delivery lines 6, 7, a nonreturn valve 8, a shut-off valve 10, a throttle 9 and a pressure reducer 11. The lifting cushions 1, 3 can be depressurized via a ventilating valve 13 connected to the delivery lines 6, 7.

In the preferred embodiment, the first lifting cushion 1 supports the patient 4 in the head and shoulder region, while the second lifting cushion 3 is in contact with the patient's back in the lumbar region. A part of an electrode carrier 14, which is to be placed around the chest of the patient 4, is located above the spacer 2.

The device according to the present invention operates as follows:

Together with the spacer 2, the lifting cushions 1, 3 are placed under the patient 4 before the beginning of the treatment such that the second lifting cushion 3 is in contact with the patient's back in the lumbar region. The first lifting cushion 1 will now support the head and shoulder region. If the electrode carrier 14 is to be put on the chest of the patient 4 for measurement purposes, the shut-off valve 10 is opened, and pressurized gas flows from the pressurized gas source 12 into the lifting cushions 1, 3 via the pressure reducer 11, the throttle 9 and the nonreturn valve 8. The adjustable pressure reducer 11 limits the filling pressure to about 200 mbar. When the lifting cushions 1, 3 have lifted the patient 4 by about 5 cm, the shut-off valve 10 is closed. A cavity has formed under the patient 4 in the area of the spacer 2, and the electrode carrier 14 can be pulled manually through the cavity under the patient 4 and then positioned on the upper body. The patient is then lowered by opening the ventilating valve 13. The lifting height of the lifting cushions 1, 3 can be set by changing the back pressure of the pressure reducer 11.

The device according to the invention may have cushions 1, 3 that are formed of a single gas cell or by multiple connected cells, isolated cells or cells fed by one or more manifold. The cushions 1, 3 form a system with an existing patient bed 5 in the embodiment of the FIGURE. The cushions (the structure defining one gas cell or a group of gas cells) may also be incorporated in the patient bed 5 or be part of a unit (including a cover or section piece) that interacts with the patient bed 5.

While a specific embodiment of the invention has been shown and described in detail to illustrate the application of the principles of the invention, it will be understood that the invention may be embodied otherwise without departing from such principles.

What is claimed is:

1. A device for putting an electrode carrier on a recumbent patient, the device comprising:

a first lifting cushion into which a pressurized medium is admitted, said first lifting cushion having a support means including a shoulder support portion for supporting the shoulder region of a patient and including a head support portion for supporting the head region of the patient, said support means being continuous from said head support portion to said shoulder support portion;

a second lifting cushion into which a pressurized medium is admitted, said second lifting cushion having a lumbar support means for supporting the lumbar region of the patient, said lumbar support means being adapted to extend along the lumbar region of the patient; and a spacer adapted to fix said first lifting cushion and said second lifting cushion at spaced locations in relation to one another in the chest region of the patient, said spacer defining a space between said first lifting cushion and said second lifting cushion.

2. A device in accordance with claim 1, wherein the cell width or interface width of the first lifting cushion is at least twice the cell width or interface width of the second lifting cushion.

3. A device in accordance with claim 1, wherein the spacer has a width between 5 cm and 15 cm.

4. A device in accordance with claim 1, wherein the lifting height of the lifting cushions is greater than 5 cm in the area of the spacer.

5. A device in accordance with claim 1, wherein a pressure reducer limiting the filling pressure is arranged upstream of the lifting cushions.

6. A process for putting a electrode carrier on the chest of a patient, the process comprising:

providing two lifting cushions fixed at spaced locations from one another under the patient;

admitting a pressurized medium into the lifting cushions in order to lift the patient; and pulling the electrode carrier through the free space formed between the lifting cushions.

7. A process in accordance with claim 6, wherein one of said lifting cushions extends along a lumbar region of the patient and another of said lifting cushions extends from a shoulder region to a head region of the patient.

8. A device for putting an electrode carrier on a recumbent patient, the device comprising:

a first lifting cushion that supports the shoulder region and the head of the patient at the same time and into which a pressurized medium is admitted, said first lifting cushion having a body contacting surface adapted to be in contact with the shoulder region and the head region of the patient, said body contacting surface being adapted to extend continuously from the shoulder region to the head region of the patient;

a second lifting cushion that supports the lumbar region of the patient and into which pressurized medium is admitted, said second lifting cushion having a cushion surface, said cushion surface being adapted to conform to the contour of the lumbar region of the patient; and a spacer adapted to fix the lifting cushions in relation to one another in the chest region of the patient to form a free space defined by said first lifting cushion and said second lifting cushion.

9. A device for putting an electrode carrier on a recumbent patient, the device comprising:

a first lifting cushion for supporting the shoulder region and the head of the patient at the same time and into which a pressurized medium is admitted, said first lifting cushion having a defined cell width or interface width;

a second lifting cushion for supporting the lumbar region of the patient and into which pressurized medium is admitted, said second lifting cushion having a defined cell width or interface width, said cell width or interface width of said first lifting cushion being twice the cell width or interface width of said second lifting cushion; and a spacer adapted to fix the lifting cushions in relation to one another in the chest region of the patient.

* * * * *